(12) United States Patent
Chestek et al.

(10) Patent No.: US 12,403,307 B2
(45) Date of Patent: Sep. 2, 2025

(54) CARBON FIBER IMPLANTABLE PROBE

(71) Applicant: The Regents of the University of Michigan, Ann Arbor, MI (US)

(72) Inventors: Cynthia Anne Chestek, Ann Arbor, MI (US); Elissa Joy Welle, Ann Arbor, MI (US); John Paul Seymour, Ann Arbor, MI (US); Lauren Leigh Zimmerman, Ann Arbor, MI (US); Zhonghua Ouyang, Ann Arbor, MI (US); Paras Rajni Patel, Ann Arbor, MI (US); Ahmad Jiman, Ann Arbor, MI (US); Timothy Morris Bruns, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 8 days.

(21) Appl. No.: 17/254,786

(22) PCT Filed: Jun. 21, 2019

(86) PCT No.: PCT/US2019/038500
§ 371 (c)(1),
(2) Date: Dec. 21, 2020

(87) PCT Pub. No.: WO2019/246536
PCT Pub. Date: Dec. 26, 2019

(65) Prior Publication Data
US 2021/0268277 A1 Sep. 2, 2021

Related U.S. Application Data

(60) Provisional application No. 62/688,762, filed on Jun. 22, 2018.

(51) Int. Cl.
*A61N 1/36* (2006.01)
*A61N 1/05* (2006.01)

(52) U.S. Cl.
CPC ....... *A61N 1/36007* (2013.01); *A61N 1/0556* (2013.01); *A61N 1/36062* (2017.08)

(58) Field of Classification Search
CPC .. A61N 1/0556; A61N 1/0553; A61N 1/0551; A61N 1/04
See application file for complete search history.

(56) References Cited

U.S. PATENT DOCUMENTS 5,158,097 A * 10/1992 Christlieb ............ A61N 1/0587
600/377
5,336,254 A * 8/1994 Brennen .............. A61N 1/0587
607/129

(Continued)

OTHER PUBLICATIONS

International Search Report corresponding to International Application No. PCT/US2019/038500, dated Oct. 8, 2019, 3 pages.

(Continued)

*Primary Examiner* — Alyssa M Alter
(74) *Attorney, Agent, or Firm* — Reising Ethington P.C.

(57) ABSTRACT

A carbon fiber implantable probe, a method of manufacturing the carbon implantable probe, and a method of implanting the probe in an implantation site, such as a nerve. The carbon fiber implantable probe includes a flexible probe body, a carbon fiber microarray (CFMA) composing one or more carbon fiber electrodes at least partially embedded in the flexible probe body, and a signal conductor connected to the one or more carbon fiber electrodes of the CFMA. In one example, the CFMA includes carbon fiber electrodes having conductive carbon cores partially surrounded by an insulative coating. The combination of the CFMA with the flexible probe body, made of silicone rubber for example, can improve implantation processes.

22 Claims, 8 Drawing Sheets

(56) References Cited

U.S. PATENT DOCUMENTS

| | | | |
|---|---|---|---|
| 8,062,300 B2 | 11/2011 | Schmitz | |
| 2003/0088301 A1* | 5/2003 | King | A61N 1/056 607/117 |
| 2006/0135862 A1* | 6/2006 | Tootle | G01N 33/4836 600/373 |
| 2008/0140195 A1 | 6/2008 | Su et al. | |
| 2010/0168830 A1 | 7/2010 | Hung | |
| 2012/0323288 A1 | 12/2012 | Anderson | |
| 2013/0211485 A1* | 8/2013 | Govindarajan | A61B 5/24 156/60 |
| 2018/0243924 A1* | 8/2018 | Visell | G01L 5/228 |

OTHER PUBLICATIONS

Written Opinion corresponding to International Application No. PCT/US2019/038500, dated Oct. 8, 2019, 5 pages.

* cited by examiner

CARBON FIBER IMPLANTABLE PROBE

GOVERNMENT FUNDING

This invention was made with government support under grant contract number OD024907 awarded by the National Institute of Health (NIH). The government has certain rights in the invention.

TECHNICAL FIELD

This invention relates to carbon fiber implantable probes, and more particularly, to carbon fiber implantable probes having a flexible body.

BACKGROUND

Long-lasting, minimally damaging, implantable probes may be used in a variety of biomedical applications, such as neural probes that interface with the peripheral nervous system. Applications for these probes range from control of robotic prostheses in cases of amputation to stimulation of autonomic nerves to regulate bladder control in cases of spinal cord injury. In addition to their stimulation capabilities, the probes may be used to record neural activity for neuroscience research or to inform the timing of applied stimulation.

Most current probes include silicon shanks that penetrate the nerve and have the potential to cause considerable damage, or cuff electrodes that wrap around the outside, potentially causing less damage but also recording less discrete nerve signals. Recent work in the field has shown that recording inside the nerve produces the best signal, and that smaller electrodes produce less damage.

SUMMARY

In accordance with one embodiment, there is provided a carbon fiber implantable probe, comprising: a flexible probe body; a carbon fiber microarray comprising one or more carbon fiber electrodes at least partially embedded in the flexible probe body; and a signal conductor connected to the one or more carbon fiber electrodes of the carbon fiber microarray.

In accordance with various embodiments, the carbon fiber implantable probe may have any one or more of the following features, either singly or in any technically feasible combination:
  the flexible probe body consists of a silicone-based material;
  the silicone-based material is a degassed silicone rubber;
  the signal conductor is at least partially embedded in the flexible probe body;
  the signal conductor is a flex array;
  each carbon fiber electrode of the one or more carbon fiber electrodes has an insulative coating;
  the insulative coating is a functionalized polymer coating;
  each carbon fiber electrode of the carbon fiber microarray has an implantation end and an attachment end, wherein the attachment end is fully embedded in the flexible probe body;
  the implantation end, the attachment end, or both the implantation end and the attachment end include an exposed portion where a conductive carbon core is exposed;
  the flexible probe body includes a plurality of discrete electrode channels for each carbon fiber electrode of the carbon fiber microarray;
  each discrete electrode channel of the plurality of discrete electrode channels joins a conductor space;
  the carbon fiber microarray is configured to be deflected so that an angle θ is produced at a body interface site, with the angle θ being located between an insertion portion of each carbon fiber electrode of the carbon fiber microarray and a plane defined by an insertion end of the flexible probe body;
  angle θ is configured to deflect between 90° and 0°, inclusive; and/or
  the angle θ is configured to deflect between 90° and 45°, inclusive.

In accordance with another embodiment, there is provided a method of manufacturing a carbon fiber implantable probe, comprising the steps of: aligning one or more carbon fiber electrodes in a carbon fiber microarray template; and partially embedding the one or more carbon fiber electrodes in a flexible probe body.

In accordance with various embodiments, the method may have any one or more of the following steps or features, either singly or in any technically feasible combination:
  degassing a silicone-based material that is used for the flexible probe body; and/or
  the degassing step is performed before the partially embedding step.

In accordance with another embodiment, there is provided a method of implanting a carbon fiber implantable probe, comprising the steps of: placing an implantation base onto a hook; using the hook to isolate an implantation site; implanting one or more carbon fiber electrodes of the carbon fiber implantable probe into the implantation site; and sealing the carbon fiber implantable probe at the implantation site.

In accordance with various embodiments, the method may have any one or more of the following steps or features, either singly or in any technically feasible combination:
  the hook is a nerve hook comprising: a shank portion and a bend portion, wherein the bend portion includes an implantation base cavity with two nerve cusps on opposite sides of the implantation base cavity; and/or
  a height of the two nerve cusps of the nerve hook is elevated with respect to the implantation base cavity.

BRIEF DESCRIPTION OF THE DRAWINGS

Preferred exemplary embodiments will hereinafter be described in conjunction with the appended drawings, wherein like designations denote like elements, and wherein.

DESCRIPTION OF THE ILLUSTRATED EMBODIMENTS

As described herein, a carbon fiber implantable probe comprises a number of carbon fiber electrodes in a carbon fiber microarray (CFMA), with the carbon fiber electrodes being at least partially embedded in a flexible body. The combination of the CFMA and the flexible body provides an unexpected increase in the resiliency and durability of the probe, as the flexible body was shown to increase the flexibility of the carbon fiber electrodes to the point where the carbon fiber electrodes were able to withstand a 90° bend at the body interface. Moreover, implantation was possible even with extreme lateral deflection of the carbon fiber electrodes. This resiliency and durability can make the implantation process easier, and it can also help maintain a better connection between the probe and the implantation site while the probe is in use. Particular implantation techniques are also described herein, which allow for the carbon fiber implantable probe to be inserted into nerves of varying diameters with minimal handling damage to the nerve during surgery. While the description below is at least generally within the context of a peripheral nervous system application, other applications are certainly possible, such as brain-based applications, spinal applications, muscle applications, or other organ-based applications.

Figure 1:
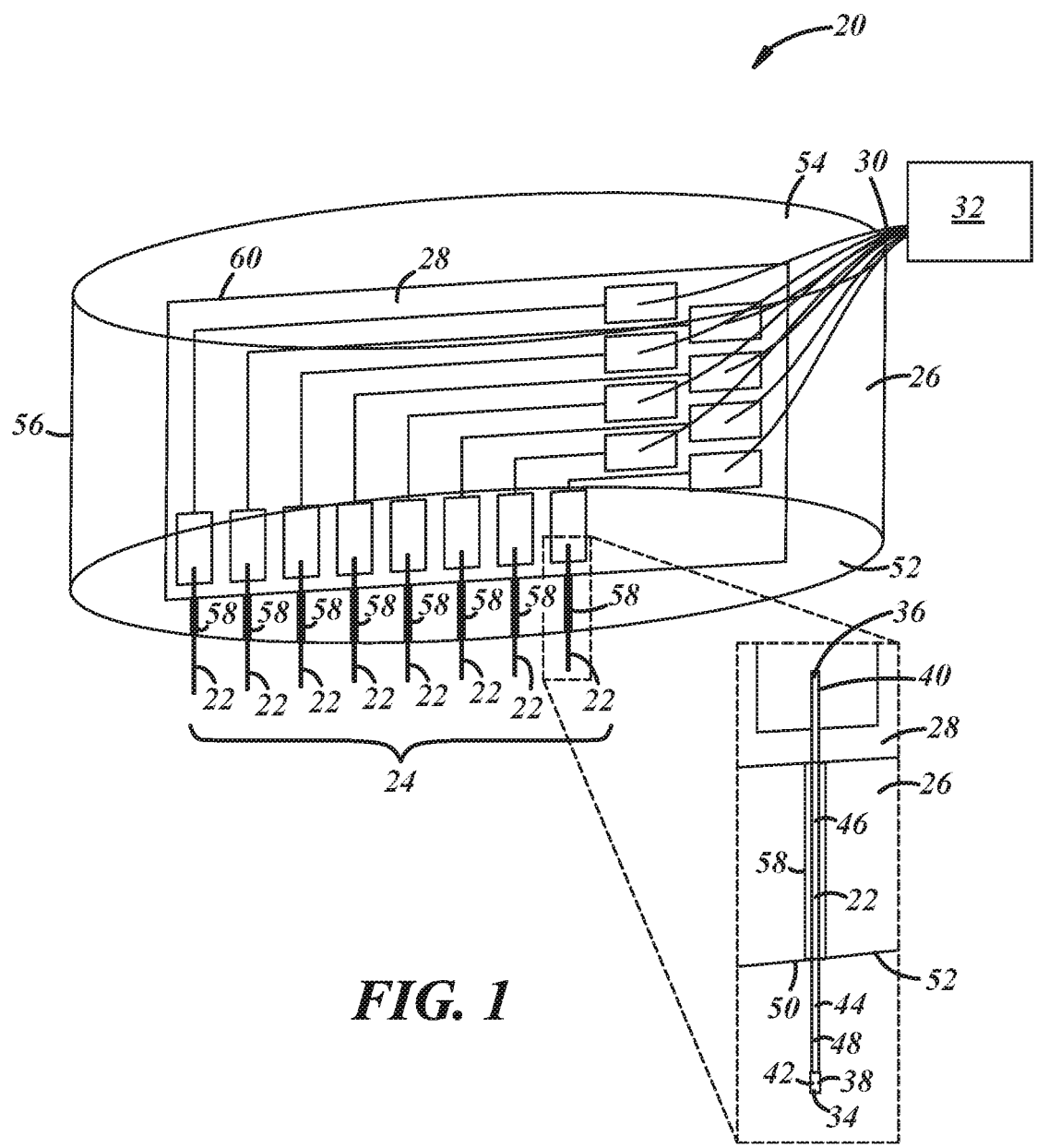
FIG. 1 is a schematic drawing of an embodiment of a carbon fiber implantable probe.

FIG. 1 is a schematic illustration of a carbon fiber implantable probe 20. The carbon fiber implantable probe 20 includes a plurality of carbon fiber electrodes 22 which together comprise a carbon fiber microarray (CFMA) 24. The carbon fiber electrodes 22 of the CFMA 24 are partially embedded in a flexible body 26. A signal conductor 28, such as a PCB, ribbon cable, or flex array with wires 30 (although it is certainly possible to have a wireless implementation with a WiFi transmitter or the like used as the signal conductor 28), can transmit readings to an output device 32, such as a computer or implanted device. The signal conductor 28 may also have the capability to send a stimulatory signal to one or more carbon fiber electrodes 22 of the CFMA 24. While the signal conductor 28 is shown as being embedded in the flexible body 26, other arrangements are certainly possible, such as partially-embedded or non-embedded arrangements. It should be understood that FIG. 1 is not to scale, and the relative sizes of the various components of the probe 20 are likely to vary from the illustrated embodiment. For example, the signal conductor 28 is likely to be much smaller in size as compared with the size of the flexible body 26. Similarly, the carbon fiber electrodes 22 of the CFMA 24 are likely to be much smaller in terms of length, width, etc.

FIG. 1 includes an enlarged view of one of the carbon fiber electrodes 22. The carbon fiber electrode 22 includes an implantation end 34 and an attachment end 36. The implantation end 34 may have various shapes to help encourage implantation (e.g., needle-like) or retention of the device at the implantation site. The implantation end 34 and/or the attachment end 36 may include an exposed portion 38, 40 where a conductive carbon core 42 is generally exposed. The exposed portion 38, 40 is generally free of a thin, functionalized polymer coating 44 that may be used to insulate one or more portions of the conductive carbon core 42. The exposed portion 38 at the implantation end 34 may facilitate signal transmission for neuromodulation. The exposed portion 38 at the attachment end 36 may also facilitate signal transmission via connection to the signal conductor 28, such as a flex array. This connection, in some embodiments, may be accomplished with a conductive silver epoxy or a metal solder with a low melting temperature, such as indium, to cite a few examples. In other embodiments, the signal conductor 28 may be more integrally formed, patterned, layered, or the like with the conductive carbon core 42. It is possible as well to have additional exposed portions 38, 40, or to locate exposed portions at different locations along the carbon fiber electrode 22. For example, multiple exposed portions may be situated along the exposed length of the carbon fiber electrode 22.

The carbon fiber electrode 22 includes an embedded portion 46 that is generally surrounded by the flexible body 26 and an insertion portion 48 that extends beyond the flexible body 26. In some embodiments, the insertion portion 48 is about 25-500 μm, preferably 100-250 μm. In some embodiments, the length of the insertion portion 48 varies between the different carbon fiber electrodes 22 in the CFMA 24 in order to accommodate insertion into nerves of different diameters or to access different depths or fascicles within a nerve. The carbon fiber electrode 22 may have a diameter at the embedded portion 46, the insertion portion 48, or both, of less than 9 μm, and in some embodiments, is about 5 μm. In some embodiments, the carbon fiber electrode 22 has an aspect ratio (defined as a length of the longest axis divided by the diameter), which is preferably about 100 and in certain implementations, greater than about 1,000, or in some embodiments, greater than 10,000. A body interface site 50 is situated between the embedded portion 46 and the insertion portion 48 where the carbon fiber electrode 22 exits the flexible body 26. As will be detailed further below, the flexible body 26 and carbon fiber electrode 22 combination can result in angles at the body interface site 50 between the embedded portion 46 and the insertion portion 48 of up to 90°.

The conductive carbon core 42 may have the form of an elongated wire that spans the length of the carbon fiber electrode 22 from the implantation end 34 to the attachment end 36. In an advantageous embodiment, the conductive carbon core 42 comprises one or more carbon fibers. In a particular implementation, the conductive carbon core 42 consists of Cytec Thorne™ T-650/35 3K carbon fiber, polyacrylonitrile (PAN) precursor. A resin matrix composite is used to treat the fiber surface, which can increase the interlaminar shear strength. In this embodiment, the conductive carbon core 42 has a 1.75% elongation at break, a modulus of elasticity of about 241 GPa, an electrical resistivity of about 0.00149 ohm-cm, and a thermal conductivity of 14.0 W/m-K. In other embodiments, the conductive carbon core 42 may be comprised of a carbon fiber having 1-5% resin (or more particularly about 2% resin), glassy carbon microstructures, carbon nanotubes (CNTs), metallic CNTs, or a CNT composite. Certain desirable carbon fibers can have a modulus of elasticity of greater than or equal to about 200 GPa, for example between 240 GPa to about 999 GPa.

The coating 44 on the carbon fiber electrodes 22 may be an insulative coating; however, in some embodiments, a coating may not be used at all, and one or more of the carbon fiber electrodes 22 may be uncoated. An uncoated carbon fiber electrode 22 may be used in implementations where the flexible body 26 is sufficiently insulative. The coating 44 is advantageously deposited, such as via a chemical vapor deposition (CVD) process, a micro-patterning process, or another suitable coating process. In one embodiment, the coating consists of parylene, or more particularly, parylene-c. In another embodiment, the coating includes functionalized poly-p-xylylenes. Poly(3,4-ethylenedioxythiophene):p-toluene sulfonate (PEDOT:pTS) may be selectively coated onto one or more areas of the carbon fiber electrode 22, such as at the exposed portion 38 and/or the implantation end 34. In some embodiments, only selected areas are coated, such as embodiments having multiple exposed portions along the insertion portion 48. For example, platinum black may be selectively electrodeposited as recording sites on the insertion portion 48 of the conductive carbon core 42. In one embodiment, the conductive carbon core 42 is nominally about 5 μm on a side or in diameter, and has a coating layer that is about 0.5-1 μm thick. Other coating materials, processes, and/or coating configurations are certainly possible.

A plurality of carbon fiber electrodes 22 form the carbon fiber microarray (CFMA) 24. As shown in FIG. 1, the CFMA 24 may include a relatively straight line of carbon fiber electrodes 22 that are evenly spaced or distributed in the flexible body 26. This configuration may be advantageous for minimally invasive methods of PNS neuromodulation. In other embodiments, the CFMA 24 may have a different configuration. For example, the carbon fiber electrodes 22 may be clustered in brain or organ-based implementations. However, the line configuration is desirable in embodiments where the probe 20 is used to obtain readings from a single nerve or neuron. In some embodiments, carbon fiber electrodes 22 in a CFMA 24 may have lateral offsets (1-200 μm between electrodes) to interface with different clusters of neurons across the span or width of a nerve. Further, the CFMA 24 may have more or less carbon fiber electrodes 22 than what is schematically illustrated in FIG. 1.

The flexible body 26 works unexpectedly well with the CFMA 24. As opposed to typical or standard silicon shanks or probes, which are comparatively much more rigid, the flexible body 26 increases the flexibility of the carbon fiber electrodes 22 to the point where the electrodes can withstand a 90° bend at the body interface site 50. "Flexible," when used to describe the body 26, means that the body is comprised of a rubber or thermoset elastomer (TSE) in one embodiment. In a preferred embodiment, the flexible body 26 is silicone, or even more preferably, A-103 Medical Grade Elastomer from Factor II, Inc. This particular silicone is a two-component product, which, when combined, cures to a translucent silicone rubber. The elastomer component consists of a dimethylsiloxane polymer, a reinforcing silica, and a platinum catalyst. The curing agent component consists of a dimethyl-siloxane polymer, an inhibitor, and a siloxane cross linker. Other materials are certainly possible, such as parylene, polyamide, polydimethylsiloxane (PDMS), or SU-8, to cite a few examples.

In another embodiment, "flexible," when used to describe the body 26, means that the body has a modulus of elasticity between 0.000005-23 GPa. In a preferred embodiment, the body 26 has a modulus of elasticity between about 0.07 and 3 GPa. This modulus of elasticity results in a much more flexible body than comparable silicon shanks, which have a modulus of elasticity of about 60 GPa or more. In yet another embodiment, "flexible," when used to describe the body 26, means that the body has an elongation at break of about 60-1120%. In a preferred embodiment, the body 26 has an elongation at break of about 700-900%. Again, compared with typical silicon probes, which have an elongation at break that is typically less than 10%, the flexible body 26 can more resiliently support the CFMA 24.

The flexible body 26 includes an insertion end 52 and a distal end 54 with an outer side surface 56 therebetween. Other shapes are certainly possible. For example, the probe 20 could include a number of sidewalls instead of the continuous outer side surface 56. To accommodate the CFMA 24, the flexible body 26 includes a plurality of discrete electrode channels 58, each of which accommodates one of the carbon fiber electrodes 22. To accommodate the signal conductor 28, the flexible body 26 includes a conductor space 60. Each electrode channel 58 extends from the insertion end 52 to the conductor space 60. The electrode channels 58 are generally cylindrically shaped, but this may or may not vary depending on the shape of the carbon fiber electrode 22. The flexible body 26 can provide for a more stress-resistant electrode channel 58, allowing for relative movement between the CFMA 24 and the insertion end 52 at each body interface site 50.

Figure 2A:
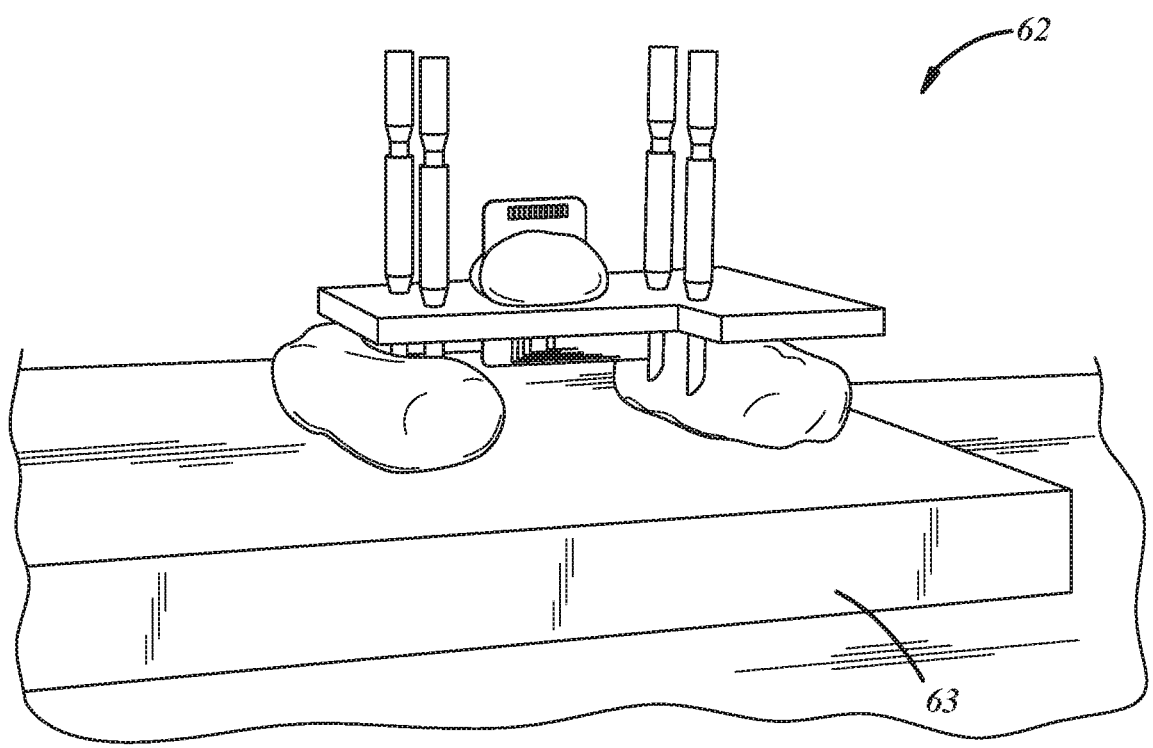
FIGS. 2A and 2B show an embodiment of a carbon fiber microarray (CFMA) template that may be used in the manufacturing method of a carbon fiber implantable probe, such as the probe of FIG. 1.
Figure 2B:
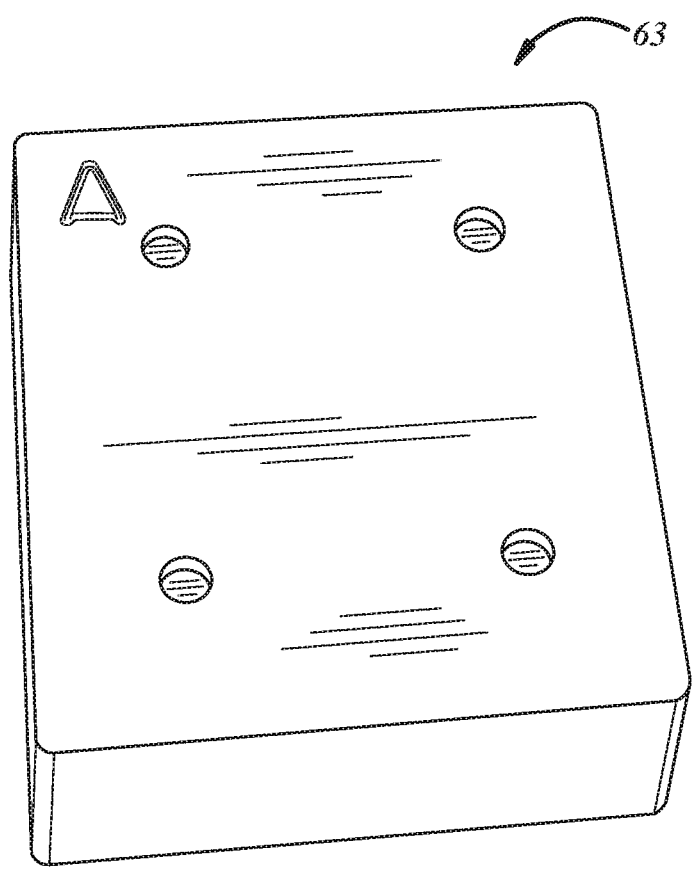

To manufacture the carbon fiber implantable probe 20, a CFMA template 62, one example of which is shown in FIG. 2A, may be used. The CFMA template 62 may align the carbon fiber electrodes 22 in the CFMA 24 while they are embedded in the flexible body 26. The CFMA template 62 is a zero insertion force (ZIF) board, which is positioned over a mold 63. An enlarged view of the mold 63 is shown in FIG. 2B. The carbon fiber electrodes 22 are mounted to the ZIF board for alignment purposes with silver epoxy and extend to a length of about 1.5 mm. The mold 63 for the flexible body 26 is an aluminum sheet with a plurality drilled depressions for a silicone flexible body, is filled with the body material to embed the CFMA 24. The mold 63 can be coated with a thin layer of lubrication jelly to facilitate removal. In one embodiment, detailed below, the uncured or partially cured flexible body material is degassed. The CFMA template 62 or ZIF board is lowered into the mold until confirmation of slight fiber bending, indicating that the carbon fiber electrodes 22 have reached the depth of the mold. The uncured or partially cured material of the flexible body 26 is then cured. In one embodiment, where the flexible body 26 comprises silicone, the body material is cured for about 10-12 minutes at 115° C. Microforceps or another cutting mechanism can be run across the carbon fiber electrodes 22 at the edge of the ZIF board with applied pressure to break the carbon fiber electrodes 22 at the implantation end 34. In another embodiment, the carbon fiber electrodes are cut again to define the implantation end 34. Alternatively, the CFMA template 62 may be an SU-8 jig or some other apparatus to properly position the carbon fiber electrodes 22. In yet other embodiments, the CFMA template 62, the probe 20, and/or the flexible body 26 is 3D printed. Other manufacturing processes are certainly possible.

In some embodiments, the flexible body 26 comprises a degassed silicone. When the silicone is heated to cure, air bubbles in the silicone can expand, and if these air bubbles are in the vicinity of the carbon fiber electrodes 22, the carbon fiber electrodes 22 may move from their originally straight position. Degassing the silicone allows for the formation of a straight electrode channel 58 to accommodate a straight carbon fiber electrode 22. Further, the degassed silicone has a higher density which can provide more structural support for the CFMA 24. In one embodiment, during the manufacturing process, filled molds are degassed in a vacuum chamber for approximately 40-60 minutes with periodic vacuum release until the visible bubbles are gone. The CFMA template 62, such as the ZIF board described above, can then be aligned above the mold and then lowered into the uncured material of the flexible body 26 and held in the body until the material is cured. Degassing can be accomplished before or after embedding. Before embedding may be preferred in some instances, as the degassing process may cause the carbon fiber electrodes 22 to be shifted from their straight position orthogonal to the insertion end 52 of the flexible body 26.

Figure 3A:
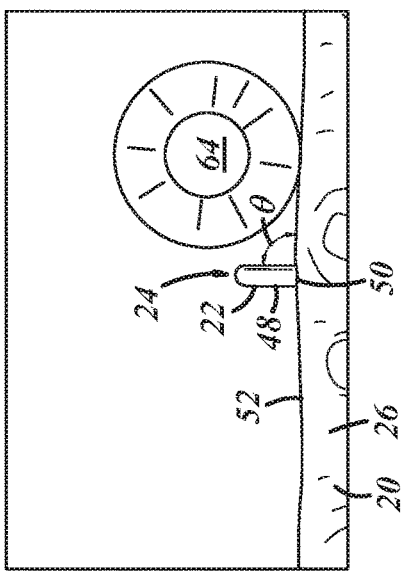
FIGS. 3A-3C illustrate the capability of the carbon fiber implantable probe to withstand extreme lateral motion, with FIG. 3A showing the carbon fiber microarray (CFMA) before being exposed to a laterally traversing force, FIG. 3B showing the CFMA while exposed to the laterally traversing force, and FIG. 3C showing the CFMA after exposure to the laterally traversing force.
Figure 3B:
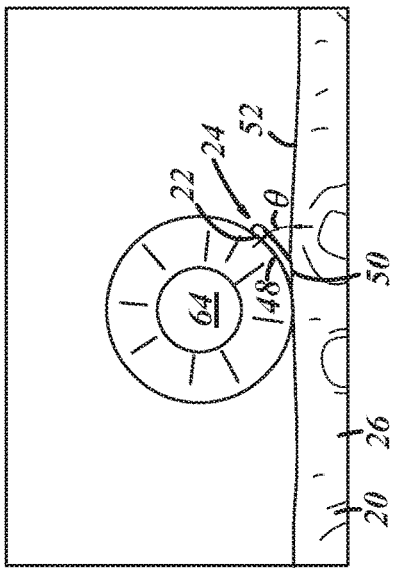
Figure 3C:
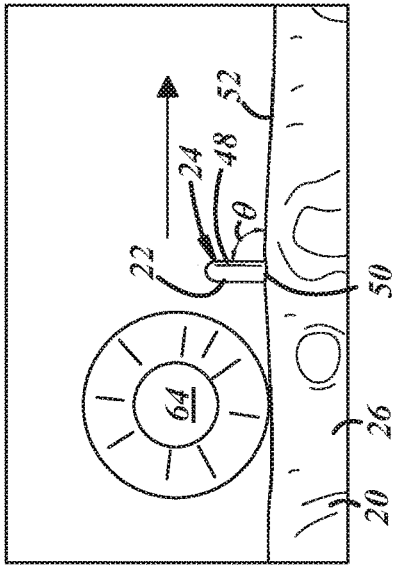

FIGS. 3A-3C show how the flexible body 26 can increase the durability of the carbon fiber electrodes 22 (only one is labeled in each of FIGS. 3A-3C for clarity purposes), thereby increasing the surgical implementation capability of the CFMA 24. In this embodiment, the insertion portion 48 of each of the carbon fiber electrodes 22 is 245 μm. A glass capillary 64 was laterally moved across the insertion end 52 of the flexible body 26. The size of the capillary 64 was chosen to approximate the size of a large nerve. FIG. 3A shows the CFMA 24 before contact with the capillary 64. FIG. 3B shows the CFMA 24 as its being deflected by the capillary 64. As shown, the CFMA 24 is deflected such that an angle θ is produced at the body interface site 50, with the angle θ being located between the insertion portion 48 of each carbon fiber electrode 22 and a plane defined by the insertion end 52 of the body 26. The angle θ was able to change from 0°, to about 45° as shown in FIG. 3B, to 90°, and then back to 0° as shown in FIG. 3C. The CFMA 24 was unharmed after a 90° deflection.

Figure 4A:
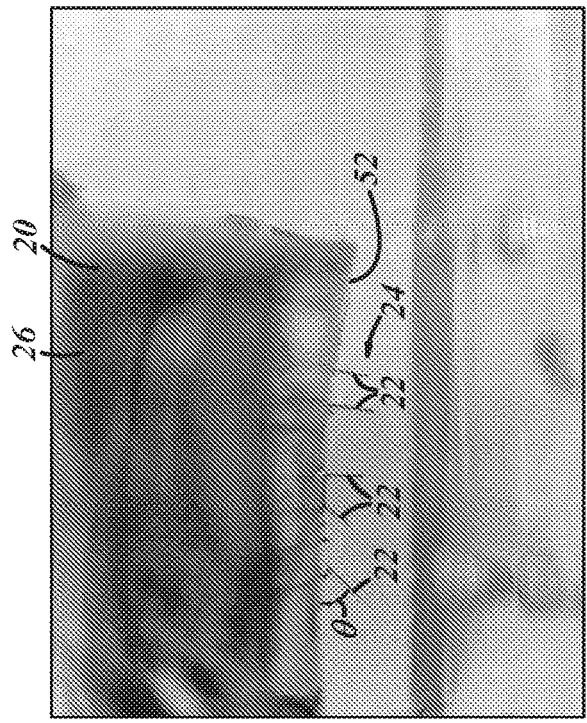
FIGS. 4A and 4B illustrate an embodiment of a carbon fiber implantable probe, with FIG. 4A showing a CFMA before forced breakage and FIG. 4B showing the CFMA after forced breakage.
Figure 4B:
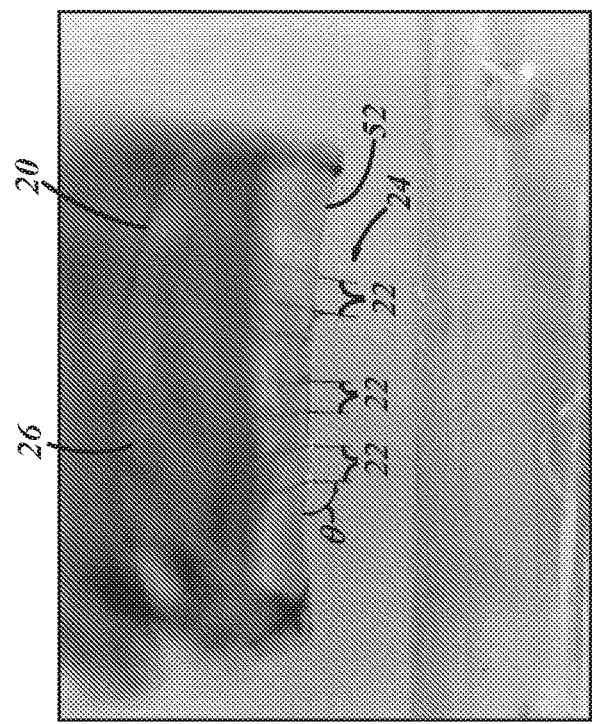
Figure 5A:
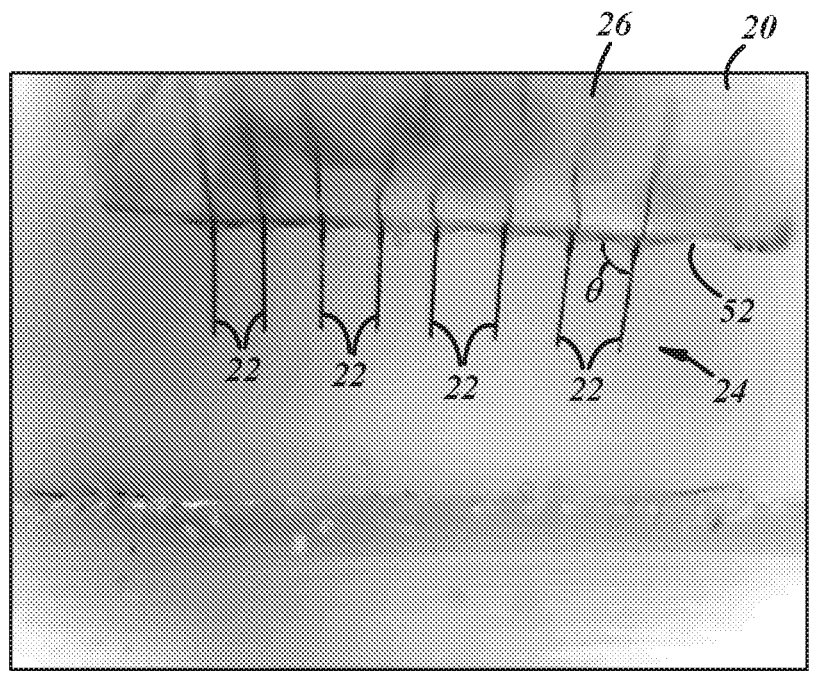
FIGS. 5A and 5B illustrate another embodiment of a carbon fiber implantable probe, with FIG. 5A showing a CFMA before forced breakage and FIG. 5B showing the CFMA after forced breakage.
Figure 5B:
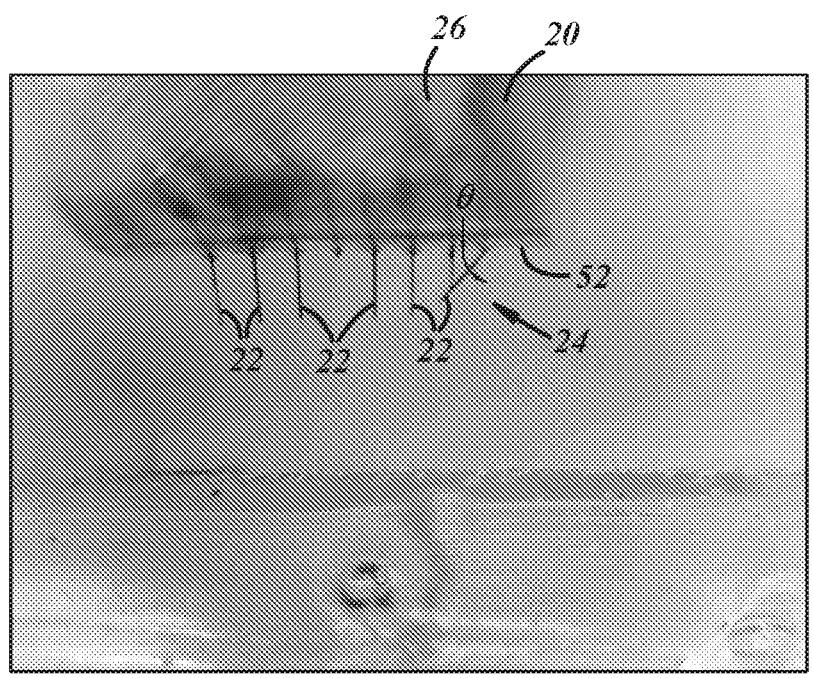

FIGS. 4A-4B and 5A-5B also show how the flexible body 26 can increase the durability of the carbon fiber electrodes 22. In FIGS. 4A and 4B, the CFMA 24 is approximately 125 μm long. In FIGS. 5A and 5B, the CFMA 24 is approximately 200 μm long. FIGS. 4A and 5A show each CFMA 24, respectively, before a forced breakage of a plurality of the carbon fiber electrodes 22. Each CFMA 24 was then exposed to a breaking force, which caused the carbon fiber electrodes 22 to be oriented at various angles θ relative to the insertion end 52, or in some cases, caused the carbon fiber electrodes 22 to be broken off altogether. FIGS. 4B and 5B show each probe 20 after forced breakage. Unexpectedly, both probes in FIGS. 4B and 5B, with the various angles θ, were successfully implanted.

Figure 6:
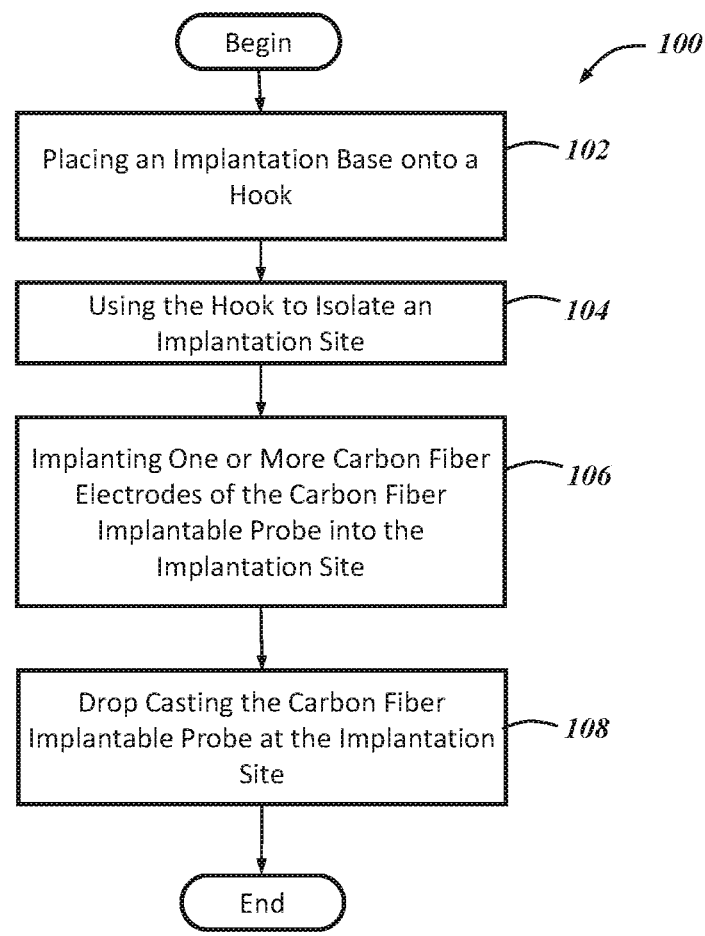
FIG. 6 is a flowchart illustrating an example embodiment of a method of implanting a carbon fiber implantable probe, such as the carbon fiber implantable probe of FIG. 1.
Figure 7:
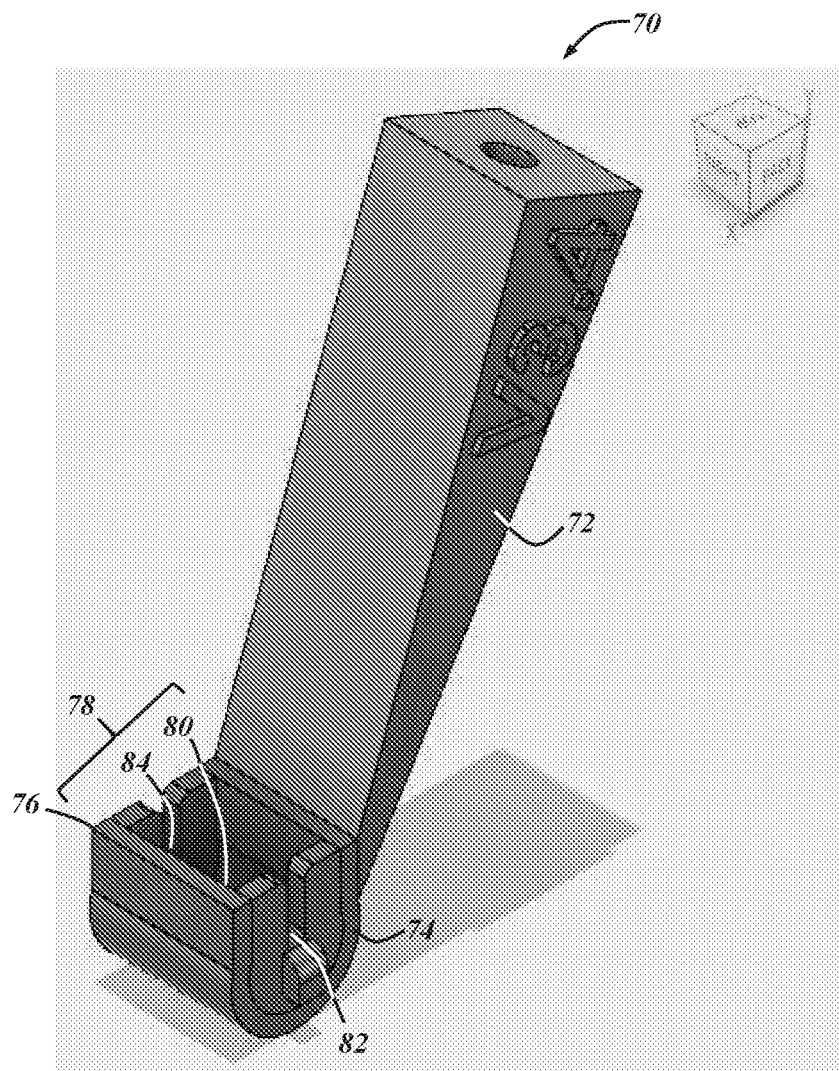
FIG. 7 shows a nerve hook that may be used to isolate the nerve for implantation.

FIG. 6 is a flowchart illustrating example steps of a method 100 of implanting a carbon fiber implantable probe, such as the carbon fiber implantable probe 20 schematically illustrated in FIG. 1. Step 102 involves placing an implantation base onto a hook, which is an optional step. An example hook is the nerve hook 70 illustrated in FIG. 7. The nerve hook 70 includes a shank portion 72 and a bend portion 74. The bend portion 74 ends at a tip 76 such that a gap 78 exists between the tip 76 and the shank portion 72. The length of the gap 78 may vary and can depend on the size of the target nerve for implantation. The size of gap 78 also allows for ample space from above for the probe 20 to be inserted. The bend portion 74 includes an implantation base cavity 80 for placing the implantation base, such as a silicone piece, that is used later in the method 100 for implanting the carbon fiber implantable probe 20. Two opposing walls of the implantation base cavity 80 include nerve cusps 82, 84, which can help position an isolated nerve. Alternatively, the base cavity 80 may have a deeper recession, or well, that allows drop casted material to flow around the nerve and probe 20. The height of the nerve cusps 82, 84 may be elevated relative to the base cavity 80 to provide greater isolation of the nerve to potentially minimize water interference on the nerve surface during insertion. This height may be adapted in various nerve hook embodiments to account for dimensions of the implantation site or other surgical considerations.

Figure 8:
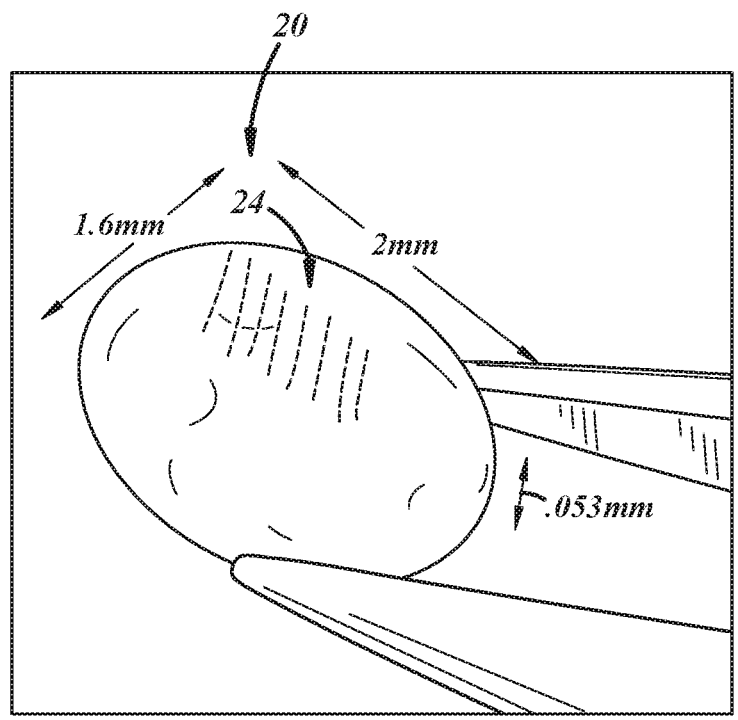
FIG. 8 is an image of a CFMA.
Figure 9:
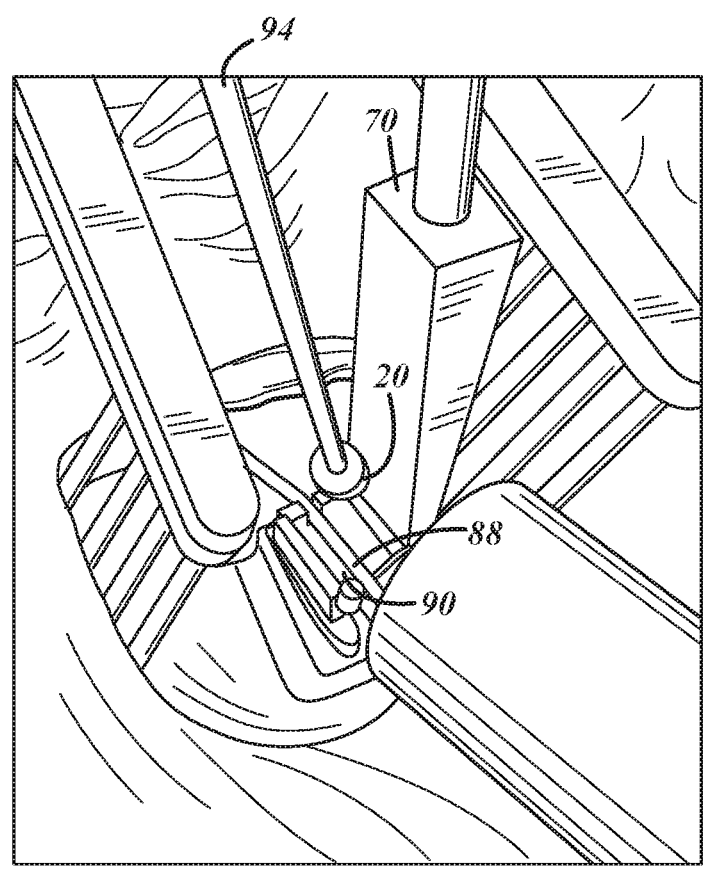
FIG. 9 is an image of surgical placement using the CFMA of FIG. 8 that may be used with the implanting method of FIG. 6.
Figure 10:
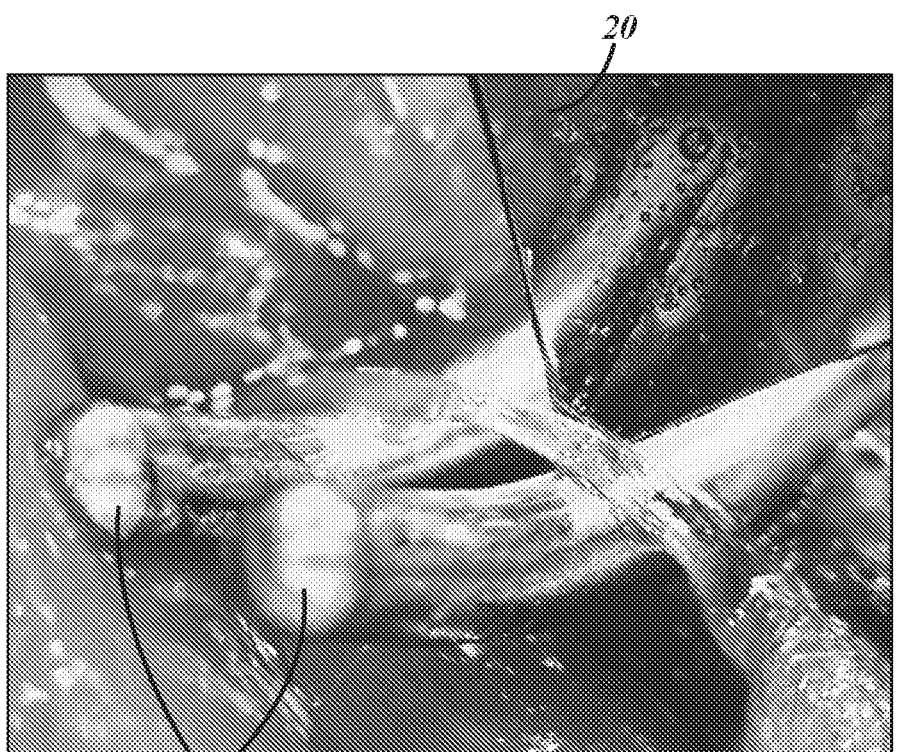
FIG. 10 shows an embodiment of a carbon fiber implantable probe as it is being inserted into a nerve.

Step 104 of the implantation method 100 involves using the hook 70 to isolate an implantation site. FIG. 8 shows the probe 20, and FIG. 9 shows surgical placement of the non-functional probe 20 of FIG. 8 into a rat cervical vagus nerve. The nerve hook 70 is lowered toward the implantation site and used to lift the vagus nerve from the surrounding tissue. FIG. 9 is an enlarged view of the implantation site 88, as hooked by the hook 70 with an optional implantation base 90. FIG. 10 shows another embodiment of a hook. In this embodiment, a dual-pronged glass hook 92 is used to isolate the implantation site. Since it may be difficult to hold an implantation base with the glass hook 92, the nerve hook 70 may be preferred in surgeries where an implantation base is not necessary or desired. Other implantation assist devices are certainly capable of being used.

Returning to FIG. 6, step 106 of the implantation method 100 involves implanting one or more carbon fiber electrodes 22 of the CFMA 24 of the probe 20 into the implantation site, such as the implantation site 88. The probe 20 can be carried by a suction wand 94 at the distal end of the body and lowered toward the hook 70, as shown in FIG. 9. A small blunt needle tip attached to the suction wand 94 may be used to pick up the probe 20. As described above, the flexible body 26 allows for greater implantation and surgical freedom, as bending or breaking of one or more of the carbon fiber electrodes 22 can be tolerated without undesirably impacting the recording and/or stimulating capabilities of the probe 20.

Figure 11:
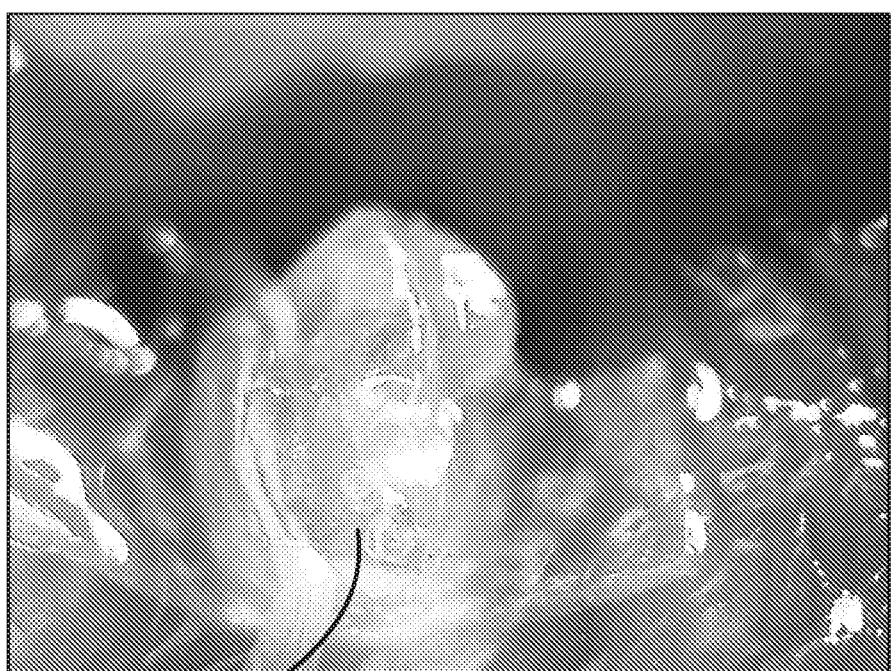
FIG. 11 shows an example embodiment of an implanted carbon fiber implantable probe.

Step 108 of the method involves sealing the probe 20 to the nerve at the implantation site 88 using a drop cast sealant. FIG. 11 shows a casted implantation site 96 where a biocompatible liquid silicone has been applied to the nerve hook 70, covering both the flexible body 26 of the probe 20, as well as the implantation base 90, thereby sealing the probe 20 and implantation base 90. In one embodiment, Kwik-Sil™ is used to seal the probe 20 to the nerve. In another embodiment, fibrin glue is used to seal the probe 20 to the nerve. If a needle tip is used to initially help pick up the probe 20, the needle tip may be removed from the probe during the curing process. After curing, the implanted nerve and casted implantation site 96 are lifted off the nerve hook 70 and placed back in the cavity. Other steps are certainly possible, such as using a removable PEG layer on an insertion rod to insert the probe 20, tying off pre-sewn sutures for additional stability after drop casting, or wrapping the cast implantation site and nerve with a porcine wrap, to cite a few examples.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A carbon fiber implantable probe, comprising:
   a flexible probe body;
   a carbon fiber microarray comprising a plurality of carbon fiber electrodes at least partially embedded in the flexible probe body, wherein each carbon fiber electrode of the carbon fiber microarray has an implantation end and an attachment end, wherein the attachment end is fully embedded in the flexible probe body and the implantation end is fully exposed and separated from the flexible body, wherein, for each of at least some of the carbon fiber electrodes, the implantation end and attachment end are spaced by a distance equal to a longest length of the carbon fiber electrode, wherein a body interface site is formed where each carbon fiber electrode of the carbon fiber microarray exits the flexible probe body, and wherein the flexible probe body allows for relative movement between the carbon fiber microarray and an insertion end of the flexible probe body at each body interface site, wherein one or more carbon fiber electrodes of the plurality of carbon fiber electrodes are moveable with respect one or more other carbon fiber electrodes of the plurality of carbon fiber electrodes, wherein the carbon fiber microarray is configured to implant one or more of the carbon fiber electrodes between the insertion end and the flexible probe body into an implantation site, and wherein the flexible probe body is flexible at the insertion end where each carbon fiber electrode of the carbon fiber microarray exits the flexible probe body, wherein flexible is a material having a modulus of elasticity between 0.000005 GPa and 23 GPa; and
   a signal conductor connected to the one or more carbon fiber electrodes of the carbon fiber microarray.

2. The carbon fiber implantable probe of claim 1, wherein the flexible probe body consists of a silicone-based material.

3. The carbon fiber implantable probe of claim 2, wherein the silicone-based material is a degassed silicone rubber.

4. The carbon fiber implantable probe of claim 1, wherein the signal conductor is at least partially embedded in the flexible probe body.

5. The carbon fiber implantable probe of claim 4, wherein the signal conductor is a flex array.

6. The carbon fiber implantable probe of claim 1, wherein each carbon fiber electrode of the one or more carbon fiber electrodes has an insulative coating.

7. The carbon fiber implantable probe of claim 6, wherein the insulative coating is a functionalized polymer coating.

8. The carbon fiber implantable probe of claim 1, wherein the implantation end, the attachment end, or both the implantation end and the attachment end include an exposed portion where a conductive carbon core is exposed.

9. The carbon fiber implantable probe of claim 1, wherein the flexible probe body includes a plurality of discrete electrode channels for each carbon fiber electrode of the carbon fiber microarray.

10. The carbon fiber implantable probe of claim 9, wherein each discrete electrode channel of the plurality of discrete electrode channels joins a conductor space.

11. The carbon fiber implantable probe of claim 1, wherein the carbon fiber microarray is configured to be deflected so that an angle θ is produced at the body interface site, with the angle θ being located between an insertion portion of each carbon fiber electrode of the carbon fiber microarray and a plane defined by the insertion end of the flexible probe body.

12. The carbon fiber implantable probe of claim 11, wherein the angle θ is configured to deflect between 90° and 0°, inclusive.

13. The carbon fiber implantable probe of claim 12, wherein the angle θ is configured to deflect between 90° and 45°, inclusive.

14. A method of implanting the carbon fiber implantable probe of claim 1, comprising the steps of:
   placing an implantation base onto a hook, wherein the implantation base is separate from the carbon fiber implantable probe;
   using the hook to isolate the implantation site;
   implanting one or more carbon fiber electrodes of the carbon fiber implantable probe into the implantation site; and
   sealing the carbon fiber implantable probe at the implantation site.

15. The method of claim 14, wherein the hook is a nerve hook comprising:
   a shank portion; and
   a bend portion, wherein the bend portion includes an implantation base cavity with two nerve cusps on opposite sides of the implantation base cavity, wherein the implantation base is placed into the implantation base cavity in the bend portion of the nerve hook.

16. The method of claim 15, wherein a height of the two nerve cusps of the nerve hook is elevated with respect to the implantation base cavity.

17. The carbon fiber implantable probe of claim 1, wherein the plurality of carbon fiber electrodes includes eight or more carbon fiber electrodes.

18. The carbon fiber implantable probe of claim 1, wherein each carbon fiber electrode of the plurality of carbon fiber electrodes has an aspect ratio which is greater than 1,000.

19. The carbon fiber implantable probe of claim 18, wherein each carbon fiber electrode of the plurality of carbon fiber electrodes has an aspect ratio which is greater than 10,000.

20. The carbon fiber implantable probe of claim 1, wherein a length of the insertion portion varies between one or more carbon fiber electrodes of the plurality of carbon fiber electrodes.

21. A method of manufacturing a carbon fiber implantable probe, comprising the steps of:
aligning a plurality of carbon fiber electrodes in a carbon fiber microarray template;
degassing a silicone-based material that is used for a flexible probe body; and
partially embedding the plurality of carbon fiber electrodes in the flexible probe body after aligning the plurality of carbon fiber electrodes in the carbon fiber microarray template to form a carbon fiber microarray that is at least partially embedded in the flexible probe body, wherein a body interface site is formed where each carbon fiber electrode of the carbon fiber microarray exits the flexible probe body, and wherein the flexible probe body allows for relative movement between the carbon fiber microarray and an insertion end of the flexible probe body at each body interface site, wherein one or more carbon fiber electrodes of the plurality of carbon fiber electrodes are moveable with respect one or more other carbon fiber electrodes of the plurality of carbon fiber electrodes, wherein the carbon fiber microarray is configured to implant one or more of the carbon fiber electrodes between the insertion end and the flexible probe body into an implantation site, and wherein the flexible probe body is flexible at the insertion end where each carbon fiber electrode of the carbon fiber microarray exits the flexible probe body, wherein flexible is a material having a modulus of elasticity between 0.000005 GPa and 23 GPa.

22. The method of claim 21, wherein the degassing step is performed before the partially embedding step.

* * * * *